(12) United States Patent
Rzany et al.

(10) Patent No.: US 11,571,495 B2
(45) Date of Patent: Feb. 7, 2023

(54) MEDICAL MATERIAL AND METHOD FOR PREPARING FROM BIOLOGICAL TISSUE

(71) Applicant: BIOTRONIK AG, Buelach (CH)

(72) Inventors: Alexander Rzany, Nuremberg (DE); Wilhelm Erdbruegger, Dortmund (DE); Tobias Kissling, Bern (CH); Tobias Igelspacher, Erlangen (DE); Bernhard Hensel, Erlangen (DE)

(73) Assignee: BIOTRONIK AG, Buelach (CH)

( * ) Notice: Subject to any disclaimer, the term of this patent is extended or adjusted under 35 U.S.C. 154(b) by 43 days.

(21) Appl. No.: 16/340,936

(22) PCT Filed: Nov. 6, 2017

(86) PCT No.: PCT/EP2017/078351
§ 371 (c)(1),
(2) Date: Apr. 10, 2019

(87) PCT Pub. No.: WO2018/083305
PCT Pub. Date: May 11, 2018

(65) Prior Publication Data
US 2019/0224369 A1 Jul. 25, 2019

(30) Foreign Application Priority Data
Nov. 7, 2016 (EP) .................................. 16197530

(51) Int. Cl.
*A61L 27/36* (2006.01)
*A61L 27/24* (2006.01)
*A61L 27/56* (2006.01)
*A61L 27/50* (2006.01)

(52) U.S. Cl.
CPC ........... *A61L 27/3633* (2013.01); *A61L 27/24* (2013.01); *A61L 27/3687* (2013.01); *A61L 27/507* (2013.01); *A61L 27/56* (2013.01); *A61L 2430/20* (2013.01); *A61L 2430/40* (2013.01)

(58) Field of Classification Search
CPC .. A61L 27/3633; A61L 27/24; A61L 27/3687; A61L 27/507; A61L 27/56; A61L 2430/20; A61L 2430/40
See application file for complete search history.

(56) References Cited

U.S. PATENT DOCUMENTS

| | | | |
|---|---|---|---|
| 5,336,616 A * | 8/1994 | Livesey | A01N 1/00 435/1.3 |
| 9,402,934 B2 * | 8/2016 | Rzany | A61L 27/367 |
| 2003/0006534 A1 * | 1/2003 | Taboas | A61F 2/30756 264/401 |
| 2010/0030340 A1 * | 2/2010 | Wolfinbarger, Jr. | A61L 27/36 623/23.72 |
| 2013/0158658 A1 | 6/2013 | Hayzlett | |
| 2014/0271784 A1 * | 9/2014 | Yang | A61K 35/28 424/443 |
| 2015/0037433 A1 * | 2/2015 | Rzany | A61L 27/367 424/569 |
| 2016/0287747 A1 * | 10/2016 | Schallenberger | A61L 27/24 |
| 2017/0119928 A1 | 5/2017 | Rzany et al. | |

FOREIGN PATENT DOCUMENTS

| | | |
|---|---|---|
| EP | 2893905 A1 | 7/2015 |
| EP | 2926840 A1 | 10/2015 |
| EP | 3165239 A1 | 5/2017 |
| WO | 2010027613 A2 | 3/2010 |

OTHER PUBLICATIONS

Pati et al., Printing three-dimensional tissue analogues with decellularized extracellular matrix bioink. Nat Commun 5, 3935, (2014), 11 pages (Year: 2014).*
Fort, Marianne; International Search Report for Application No. PCT/EP2017/07835; dated Dec. 11, 2017.
European Office Action from the corresponding European Patent Application No. 17797307, dated Sep. 29, 2020.

* cited by examiner

*Primary Examiner* — Robert A Wax
*Assistant Examiner* — Olga V. Tcherkasskaya
(74) *Attorney, Agent, or Firm* — Greer, Burns & Crain, Ltd.; Steven P. Fallon (57) ABSTRACT

Medical material and a method for preparing a biological tissue for a medical application are provided. The material is useful as a sealing element in a heart valve prosthesis. A method includes decellularizing the biological tissue by decellularizing solution to obtain an acellular extracellular matrix, solubilizing the extracellular matrix of the biological tissue, and crosslinking collagen fibers of the solubilized extracellular matrix.

14 Claims, 4 Drawing Sheets

MEDICAL MATERIAL AND METHOD FOR PREPARING FROM BIOLOGICAL TISSUE

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2017/078351, which was filed Nov. 6, 2017, which application claimed priority from European Application EP 16197530.5, which was filed Nov. 7, 2016.

FIELD OF THE INVENTION

The present invention relates to a sponge-like medical material and a method for preparing the material for medical applications, in particular for preparing material from biological tissue for use in a heart valve prosthesis (e.g. a biological heart valve prosthesis). The material is particularly useful for reducing a paravalvular leakage of such a valve prosthesis.

BACKGROUND

Such a heart valve prosthesis (also denoted as artificial heart valve) usually comprises leaflets comprising or formed out of a biological tissue which are mounted on a base body of the prosthesis. Such base body can be an expandable, particularly self-expandable stent, which is then implanted by a suitable catheter at the position of the natural defective valve that is to be replaced, particularly by the so-called transcatheter aortic valve implantation (TAVI). However other implantation approaches may also be used.

After implantation of such a heart valve prosthesis (particularly for TAVI), paravalvular leakage can occur, when blood leaks along the implanted prosthesis between the outside of the prosthesis and the vessel wall at the implantation site (e.g. in the region of the native annulus). Such leakages can lead to serious complications. Unfortunately, the severity of such a complication strongly correlates with the health condition of the patient. Hence, for weak patients sealing of paravalvular leakages is very important.

SUMMARY OF THE INVENTION

The invention provides a sponge-like medical material as well as to provide a method of preparing the material from biological tissue. A preferred sponge-like material is an extracellular matrix having a water content of 80 to 99% w/w and 40 to 90 compressibility units.

Further aspects of the present invention relate to an implant, a sealing material, as well as to a further method for preparing a material for medical application. Furthermore, the invention relates to specific uses of the material according to the present invention as well as of other materials.

A preferred method for preparing material for medical application is provided, particularly for use in a heart valve prosthesis or a stent, wherein the method includes the steps of:

providing an extracellular matrix from biological tissue and optionally decellularizing the extracellular matrix by a decellularizing solution for obtaining an acellular extracellular matrix, and solubilizing the extracellular matrix.

According to a preferred embodiment, the method further includes the following steps:

contacting the solubilized extracellular matrix with a crosslinking agent resulting in a moldable tissue suspension, and crosslinking the moldable tissue suspension, and optionally stabilized drying the obtained crosslinked material with an optional subsequent hot-pressing in order to reduce the thickness.

BRIEF DESCRIPTION OF THE DRAWINGS

Further features and advantages of the present invention and embodiments thereof shall be explained below with reference to the figure and specific examples of the present invention, wherein

FIGS. 4A and 4B show two embodiments of applying the sponge-like material to a TAVI heart valve prosthesis. In FIG. 4A the sponge-like material (textured with grey circles) is applied as a sealing ring to the outside of the valve stent by sewing or gluing.

DETAILED DESCRIPTION OF THE PREFERRED EMBODIMENTS

In preferred methods of the invention, the crosslinking may be done in molds in order to obtain materials of well-defined shape and size, e.g. bars or cylinders of several mm size. Furthermore the solubilized material can be applied layer by layer to biological material e.g. by spraying or dipping or printing or any other suitable technique for applying a substance to a material. The resulting crosslinked material surprisingly shows sponge-like behavior, i.e. the material can be compressed easily and resembles its shape after releasing the compression under wet conditions, or undergoes a further significant increase in its width and volume upon rehydration after additional stabilized drying and optional hot-pressing.

Figure 4A:
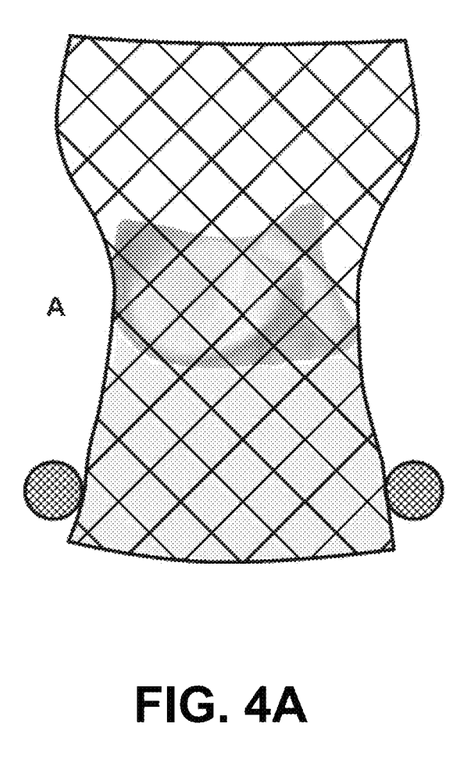
Figure 4B:
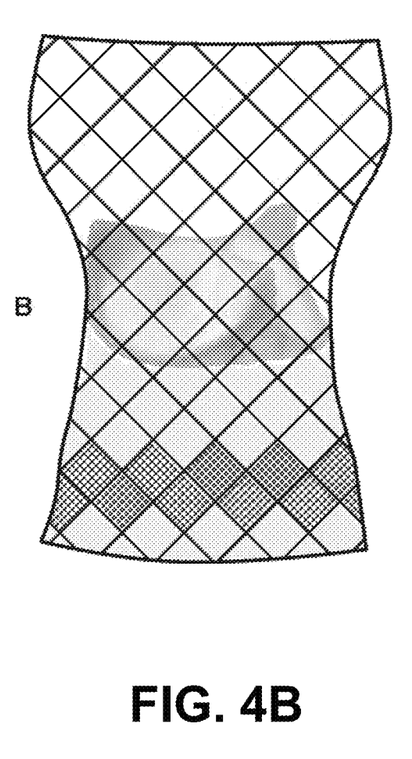
In FIG. 4B the sponge-like material is applied to the inside of the valve stent by forming tissue pockets in the conventional skirt material and filling them with the sponge-like material. Due to the sponge-like behavior the material is able to expand to the outside of the valve stent as a sealing ring.

The obtained crosslinked material exhibits solid sponge-like behavior and can be applied to (e.g. the inflow region of) a heart valve prosthesis, particularly a TAVI heart valve prosthesis. This is for example possible by filling tissue pockets with the sponge-like material or by directly fixing e.g. by sewing or gluing the sponge-like material to the implant. Two embodiments of applying the sponge-like material to a TAVI heart valve prosthesis are illustrated in FIG. 4. Therefore, the resulting material can be perfectly adapted to the prosthesis. A further embodiment includes pockets on the implant, for example in the outer skirt, wherein the moldable tissue suspension is filled and the crosslinked. Thereby an implant and in particular a heart valve prosthesis is provided having crosslinked material as provided herein, and preferably sponge-like material on the outside of the implant in pockets providing sealing against paravalvular leakage. In a further embodiment the pockets are filled with the already crosslinked sponge-like material and the pockets are sealed or glued (e.g. with the tissue glue) after the material has been placed into the pockets.

The present invention further relates to the application and manufacturing of a moldable tissue suspension prepared from optionally decellularized tissue extract, that can be applied to (e.g. the inflow region of) a heart valve prosthesis, particularly a TAVI heart valve prosthesis (e.g. by spraying or dipping) and that—after optional stabilized drying, optional hot-pressing and implantation into the body of the patient—undergoes a significant increase in thickness due to rehydration so that the prosthesis is fixed in the annulus region and is capable of sealing paravalvular leakages reliably. It shall be noted that hot-pressing is not an option if the material is already fixed to the implant; it is supposed to be done beforehand.

The possibility to manufacture a sponge-like material from an optionally decellularized biological tissue in a manner that—upon further processing—it either can be compressed easily and resembles its shape after releasing compression under wet conditions or after stabilized drying and optional hot-pressing experiences a significant increase in thickness after rehydration, allows the use of such a material to minimize paravalvular leakages, particularly in the inflow region of a TAVI heart valve prosthesis or around occluding devices such as left atrial appendage (LAA) occluder.

Innovatively, the described sponge-like material can be processed using molds of any shape. This allows obtaining tissue geometries and tissue structures not found in natural tissue, although the material is from a chemical point of view nearly identical to the crosslinked initial biological tissue. Those molds can be configured with a smooth surface to obtain tissue with a smooth surface or the molds can be configured with a structured surface to place a certain structure on the surface of the tissue. The described sponge-like material can be adapted in order to get optimal properties, e.g. for the closure of paravalvular leakages or other desired applications. Furthermore the suspension of the extracellular matrix preferably including the crosslinking agent can be provided and/or applied to implantable devices such as heart valve prosthesis by suitable methods, e.g. by applying the suspension in several layers to the prosthesis or by applying it to the prosthesis or parts thereof by immersing the latter in the solution or by attaching an already molded and three-dimensionally perfectly designed piece to the prosthesis either by gluing or sewing.

A further advantage of the present invention is the fact that the sponge-like material when formed out of decellularized biological tissue exhibits reduced thromboembolic complications and problems related to biocompatibility compared to artificial materials. Particularly, no other substances are used than those already in use for the tissue parts of implants and in particular a TAVI heart valve prosthesis. Moreover, decellularized material has that specific benefit that calcification of the material is reduced to minimum.

Particularly, regarding the method according to the invention, the original biological tissue is preferably thoroughly cleaned and prepared before implantation. In doing so, the tissue is particularly modified such that the tissue is not recognized by the body of the patient as foreign tissue. Further, the tissue is supposed not to calcify. Also, such a method for preparing tissue substantially may include at least three main steps that may have one or several intermediate rinsing processes.

Figure 3:
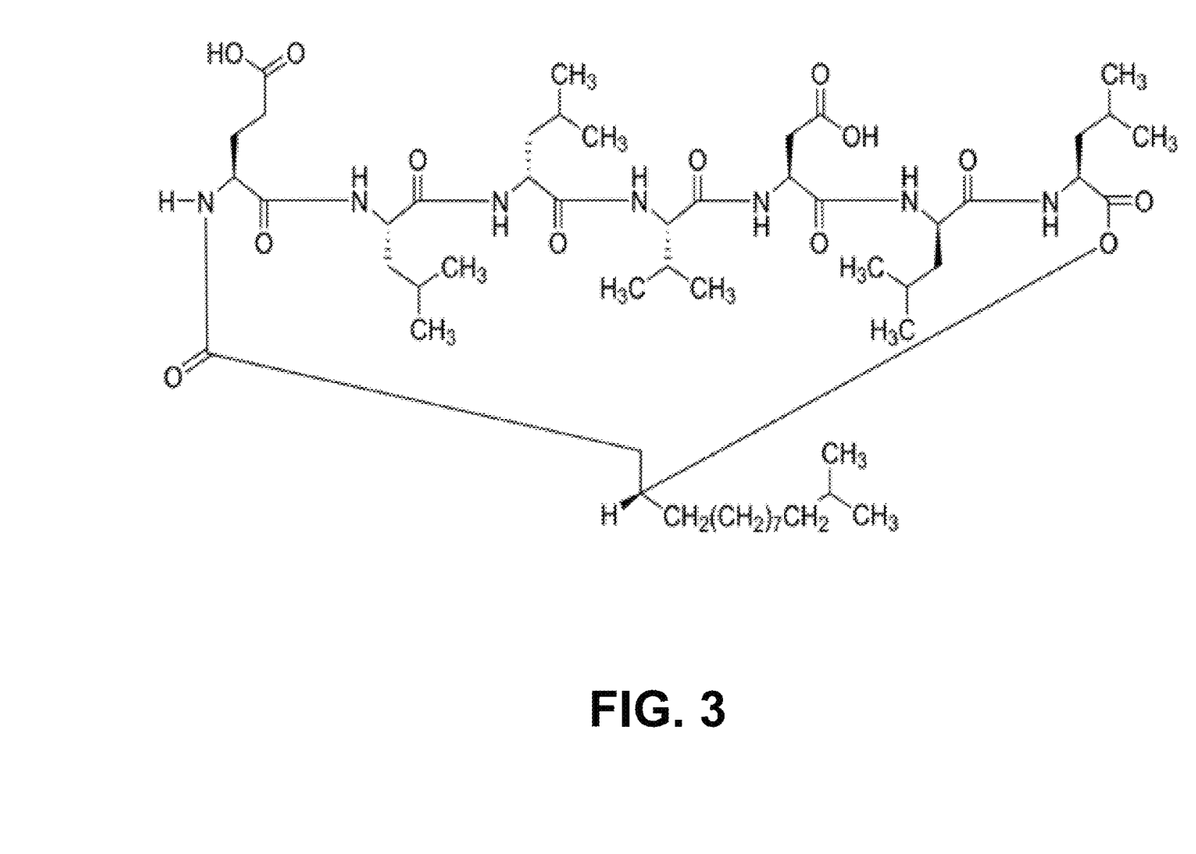
FIG. 3 is an alternative drawing of the structural formula of surfactin.

One such main preparation step that may optionally be applied according to the method described herein is the so-called decellularization of the biological tissue. In this step, cell membranes, intracellular proteins, cell nuclei, and other cellular components are removed as completely as possible from the biological tissue in order to obtain a clean extracellular matrix. Any cells and cellular components remaining in the biological tissue would be potent starting points, in particular, for undesired calcification of the biological implant material. Decellularization can be performed in different manners. The difference arises to a great extent from the decellularization agent applied. There are different kinds of decellularization agents which exhibit differing influence and impact on the tissue structure. One suitable system that is so gentle that the structure and the collagen fibers in the extracellular matrix remain as unaffected as possible while ensuring that all or almost all cells contained therein are thoroughly removed from the biological tissue includes a cyclic lipopeptide, in particular surfactin. In this preferred embodiment of the invention a surfactin-containing detergent is used for decellularization in combination with sodium deoxycholate. In particular, the detergent contains surfactin having a cyclic structure, as presented below:

Here, n=8–12, preferably 9, and Glu, Leu, Val, Asp stand for the amino acids, glutamic acid, leucine, valine and aspartic acid. An alternative drawing of surfactin's structure is provided in FIG. 3.

Lipopeptides such as daptomycin, caspofungin, arthrofactin, echinocandine, iturine, syringomycine, syringopeptide and/or polymyxin are also advantageous. The detergent expediently contains at least one lipopeptide selected from the following list: surfactin, daptomycin, caspofungin, arthrofactin or the group of echinocandine, iturine, syringomycine, syringopeptide, polymyxin. In a further preferred embodiment those gentle decellularization agents are used in combination with deoxycholate.

A further suitable system for decellularization includes sodium dodecyl sulfate (SDS, CAS Number 151-21-3). The tissue structure is changed to a bigger extent after decellularization with SDS in comparison to rather gentle decellularization agents and happens to have irreversibly changed elastin and collagen fibers in that those fibers lose their spiral configuration and adopt a linear stick-like structure. Thereby, for SDS the decellularized fibers are more elongated and the tissue structure appears to be considerably looser.

Other suitable decellularization agents are Triton X-100 and Tween 20.

Further, according to an embodiment of the present invention, the decellularizing solution includes 0.1-2% w/v sodium deoxycholate (CAS Number 302-95-4), particularly 0.5% w/v sodium deoxycholate and 0.01-0.2% w/v surfactin (CAS Number 24730-31-2, particularly 0.06% w/v surfactin in a saline solution, particularly in 0.9% w/v NaCl). Such a decellularizing solution is particularly preferred since sodium deoxycholate and surfactin can be removed very easily from the resulting tissue.

Further, according to an alternative embodiment of the present invention, the decellularizing solution includes SDS (CAS Number 151-21-3), particularly 0.1-10% w/v SDS, particularly in a saline solution (e.g. in 0.9% w/v NaCl).

Within the scope of the present application, the indication % v/v relates to a percentage by volume. Unless specified otherwise in respect of a solution, water is used as a solvent for the solutions herein. 100 ml solution with 5% v/v glutaraldehyde contains, accordingly, 5 ml glutaraldehyde. The indication % w/v relates within the scope of this application to a proportion by weight. 100 ml solution with 0.9% w/v sodium chloride contains, accordingly, 0.9 g sodium chloride.

Particularly, according to an embodiment, the biological tissue is decellularized in one of the decellularizing solutions described above for about 14 to 48 hours and particularly for 24 hours at elevated temperatures, preferably 37° C.±5° C.

Optionally, after or alternatively to primary decellularization with a suitable detergent as described herein, further treatment with at least one α-galactosidase removes remaining galactose-α-1,3-galactose-β-1,4-N-acetylglucosamine epitopes (hereinafter α-gal epitopes) from the surface of the extracellular matrix. Thereby, the risk of subsequent calcification and thromboembolic complications and problems related to biocompatibility can be significantly reduced or even minimized or completely diminished. In a preferred embodiment the tissue is treated with one α-galactosidase. However, it is likewise possible to use a combination of α-galactosidases. This means that the α-galactosidases used in combination have a different structure and/or origin; i.e. the α-galactosidases have been produced in a different living organism and/or have a different structure.

α-Galactosidases, also α-D-galactoside galactohydrolases, E.C. 3.2.1.22, are enzymes that are able to catalyze the hydrolysis of galactosyl residues of the non-reducing ends of a multiplicity of oligosaccharides and polysaccharides and also of galactolipids and glycoproteins. With regard to tissue, α-galactosidases can be used to remove α-1,3-galactosyl residues on and in the tissue. It has been found that α-gal epitopes can be effectively removed from the surface of the tissue by treatment with α-galactosidases, whereby immune responses and calcifications can be reduced.

In a preferred embodiment of the invention the extracellular matrix or the solubilized extracellular matrix are treated with at least one α-galactosidase, and preferably with an alkaline α-galactosidase. Alkaline α-galactosidases are characterized in that they have a high or their highest enzymatic activity in alkaline medium and also have a high substrate specificity. The use of alkaline α-galactosidases is advantageous, since it is thus made possible to also use DNases and RNases parallel to the alkaline α-galactosidases. DNases and RNases are used for the removal of residual ribonucleic acids from the tissue, which may also contribute to a calcium binding. By combination of α-galactosidases with DNases and/or RNases, an even more improved protection against calcification can thus be achieved, in particular in a pH range from 7.1 to 8.0, more preferably in a pH range from 7.2 to 7.8, and most preferably that demonstrate the highest specific enzyme activity in a pH range from 7.3 to 7.6. Preferred alkaline α-galactosidases originate from *Arabidopsis thaliana*, *Cucumis melo*, *Cucumis sativus*, *Oryza sativa*, for example the *Japonica* group, *Pisum sativum*, *Solanum lycopersicum*, *Tetragonia tetragonioides* and *Zea mays*. In a particularly preferred embodiment, the extracellular matrix (untreated, acellular and/or solubilized) is treated with an α-galactosidase from the GH-36 family, more preferably from the GH-36 family, sub-group II, and even more preferably from *Cucumis melo*.

Treatment of the matrix with α-galactosidase e.g. of *Cucumis melo* can exemplary be conducted by contacting the matrix with the α-galactosidase in a concentration of 1 unit per ml (1 U/ml) in DPBS at room temperature and a pH of 7.4 for 24 hours and is then rinsed with 200 ml DPBS. The rinsing process can be repeated several times if needed.

Further, according to the method of the present invention, solubilizing the extracellular matrix of the biological tissue includes one of:

chemically solubilizing the extracellular matrix, e.g. by acidic digestion. Acidic digestion can be performed e.g. in 1 N HCl for 12 h with subsequent neutralization using NaOH, centrifugation to obtain the constituents of solubilized extracellular matrix and resuspension of the pellet in 0.9% w/v NaCl to obtain a concentrated suspension;

enzymatically solubilizing the extracellular matrix, e.g. by disintegration with collagenase. Enzymatic disintegration can conducted e.g. by using 4 U/ml collagenase type IV from *clostridium histolyticum*, (Biochrom, Catalog #C4-28; other types of proteinases may also be used, especially unspecific proteinases like e.g. 'proteinase K') for 12 h in a 50 mM TES buffer (AppliChem, Catalog #A1084) containing 10 mM Ca, centrifugation to obtain the constituents of solubilized extracellular matrix and resuspension of the pellet in 0.9% w/v NaCl to obtain a concentrated suspension;

wet mechanically solubilizing the extracellular matrix, e.g. by mechanical homogenization in solution: e.g. grinding of the extracellular matrix into a suspension using a homogenizer (Bertin, Precellys Evolution) and ceramic pellets (Bertin, Catalog #CK14) in 0.9% w/v NaCl; in doing so the tissue is cooled during homogenization;

dry mechanically solubilizing the extracellular matrix in the solid state, e.g. by homogenization of the frozen extracellular matrix: e.g. by liquid Nitrogen in the form of comminuting the frozen extracellular matrix by grinding (Bertin, Precellys Evolution with ceramic pellets (Bertin, Catalog #CK14)) or manually pestling, thawing of the comminuted extracellular matrix and resuspension in 0.9% w/v NaCl.

The solubilizing by enzymatic disintegration of pericardium is best performed by use of collagenase type IV since pericardium includes a high content of dominant collagen fibers which are well digested by collagenase type IV. For other types of tissue different proteinases may be better suited such as the rather unspecific proteinase K.

Solubilizing the extracellular matrix transfers biological tissue of a (naturally) predefined shape into a form which is suitable of adopting any desired shape given that it is further processed in a specific manner as described herein. Solubilizing the extracellular matrix can further be used to clean the matrix from residual decellularization agents and residual cellular components upon centrifugation and subsequent disposal of the supernatant.

Moreover, according to one embodiment of the invention, a diluted solution of the solubilized extracellular matrix of the biological tissue (e.g. in 0.9% w/v NaCl or DPBS without Ca and Mg; Lonza, Catalog #17-512Q or another biological buffer) is provided, and wherein the solution is at first centrifuged to obtain tissue fibers and a supernatant, which can be discarded, and wherein the obtained tissue fibers are re-suspended in DPBS without Ca and Mg to obtain moldable tissue suspension.

Such procedure has the advantage that very clean material is provided for the subsequent preparative steps.

Also, it may be of particular advantage when extracellular matrices are mixed which have been solubilized by different methods to obtain moldable tissue suspension. Such embodiment has the particular advantage that the viscosity of the suspension can be fine-tuned.

Further, according to an embodiment, this moldable tissue suspension is arranged in a mold in order to generate a dimensionally (i.e. inherently) stable three-dimensional structure.

Further, according to yet another alternative embodiment, a diluted solution suspension of the solubilized extracellular matrix of the biological tissue in e.g. DPBS without Ca and Mg is provided, wherein the solution is at first centrifuged to obtain tissue fibers and a supernatant, which can be discarded, and wherein the tissue fibers are immersed in a phosphate-balanced salt solution, particularly without Ca and Mg (e.g. DPBS without Ca and Mg), wherein the fibers are particularly vortexed and mixed in the solution to obtain a homogenous slurry. The resulting homogenous slurry is contacted with the crosslinking agent, for example by admixing the slurry with 0.08-1% w/v glutaraldehyde to result a moldable tissue suspension, wherein the resulting moldable tissue suspension is then filled into a mold to form a crosslinked structure, wherein the crosslinking of the collagen fibers occurs in the mold. It is further preferred that the slurry is de-bubbled e.g. by steady and gentle shaking prior to contacting the slurry with the crosslinking agent. In a preferred embodiment of the invention crosslinking is conducted at e.g. −25° C. without movement of the moldable suspension for a time span of e.g. three days resulting material exhibiting sponge-like structure and behavior.

Optionally the crosslinked material and in particular the sponge-like material can be dried for stabilization and can be optionally hot-pressed, for example before or after being applied to an implant e.g. a heart valve prosthesis.

Also, applying a step of solubilizing as described above for manufacturing the sponge-like material according to the invention, facilitates the use of alternative tissue parts that are usually not suitable for the production of leaflets or skirt elements (e.g. due to size, thickness or other structural properties) since the original physical appearance of the tissue is destroyed. Such possibility may reduce production costs.

A further main preparation step of the method includes crosslinking the solubilized biological tissue as already indicated above, in particular and to a high extent the collagen fibers. Without being bound to theory, it is believed that crosslinking appears between the aldehyde groups of the crosslinking agent (e.g. glutaraldehyde) and amino groups naturally existing in the biological material to be crosslinked. After the material has been contacted with the crosslinking agent heat treatment results in the formation of many very stable chemical bonds between these groups of neighboring tissue fibers. Three dimensional stable structures can already be prepared by contacting the material with the crosslinking agent for a time longer than 12 hours even at temperatures below 0° C. Due to the significantly changed spatial arrangement of the tissue fibers in the decellularized and solubilized matrix compared to the native biological tissue, it is possible to increase the average distance of neighboring tissue fibers. This increased average distance and the higher flexibility result in a sponge-like material. Thereby, the method provides a new sponge-like tissue material which can adopt almost every possible shape. Additionally in wet state it can be compressed easily, resembling its shape after releasing the compression under wet conditions. Furthermore the new material shows a distinct swelling behavior by a significant increase in its thickness and volume upon rehydration after stabilized drying and optional hot-pressing.

Hence, according to an embodiment of the present invention, a diluted solution of the solubilized extracellular matrix of the biological tissue is brought in contact with a crosslinking agent. In a preferred embodiment the crosslinking agent is applied in a concentration of 0.01-5% w/v, preferably 0.08-1% w/v and more preferably 0.1 to 0.8% w/v, preferably in a phosphate-balanced salt solution. In a particularly preferred embodiment of the method the crosslinking agent is glutaraldehyde, provided with a concentration of 0.08-1% w/v, particularly 0.5% w/v, in a phosphate-balanced salt solution, particularly without Ca and Mg (e.g. in DPBS without Ca and Mg). Suitable crosslinking agents are or may contain mixtures of glutaraldehyde, carbodiimides, formaldehyde, glutaraldehyde acetals, acyl azides, cyanimide, genipin, tannin, pentagalloyl glucose, phytates, proanthocyanidines, reuterin and compounds containing epoxy groups.

In a further particular preferred embodiment, the step of contacting with the crosslinking agent and initial crosslinking is performed for 12-120 hours, preferably 48-96 hours, at temperatures below 0° C., preferably at temperatures between −5 and −40° C., and more preferably at temperatures between −15 and −30° C., preferably with a mixture containing glutaraldehyde. Material that has been contacted with the crosslinking agent under such mild condition exhibits particularly sponge-like behavior.

However, effective contacting of the solubilized extracellular matrix can also be carried out in manner such that the matrix will be well prepared for an efficient crosslinking. In a further embodiment the solubilized extracellular matrix is heated in the presence of a crosslinking agent for at least one to 20 days, preferably two to 15 days at a temperature of 25 to 60° C. more preferably in the presence of an aldehyde, even more preferably glutaraldehyde (in particular 2 days at e.g. 40° C.). Such processing will result in a high load of aldehyde groups within the solubilized extracellular matrix. The aldehyde groups can then further act upon activation as crosslinking sites between different tissue fibers.

Moreover, the inventors have found that de-bubbling and/or degassing of the solubilized suspension prior to and/or after contacting with the crosslinking agent, advantageously influences the properties in terms of elasticity and stability of the resulting sponge-like material.

Contacting the solubilized extracellular matrix may occur by directing mixing of the crosslinking agent with the matrix for example by adding a solution of the crosslinking agent to a suspension of the solubilized matrix under vigorous stirring or shaking. Contacting with the crosslinking agent may however also happen and succeed by very slow diffusion of the crosslinking agent into the solubilized material. Diffusion may be achieved by providing the crosslinking agent on one side of a (semi-)permeable barrier such as fine woven tissue or porous polymer membranes. Also, diffusion can be preferably slowed down by performing the contacting with the crosslinking agent at temperatures below 0° C., that is to frozen solubilized material. Homogeneous diffusion and distribution can be attained when the extracellular matrix is provided in the form of a suspension which has been freed from any instance that is capable of disturbing the homogeneity, for instance the suspension is degassed and/or de-bubbled prior to contacting with the crosslinking agent.

Suitable molds which allow slow diffusion of the crosslinking agent includes regions that are thus preferably (semi-)permeable for the crosslinking agent so that it can pass via the mold regions to the tissue during the crosslinking and can contact the tissue. The preferably porous mold regions or supports can have a desired or arbitrary three-dimensional shape (3D contact faces). The mold regions can be formed for example by open-pore polymer supports, which themselves do not react with the crosslinking agents (for example porous polycarbonate). For example a polymer hoses, e.g. made from PTFE can act as mold. Other suitable (porous) mold regions or support materials include, for example, sintered borosilicate glass, ceramics, or porous metals. Further, wire meshes with suitable mesh apertures such as 10 μm or with larger apertures in for instance lined in with a polymer membrane can be used as molds. The pore size, pore distribution, and mechanical properties of the support determine the feed of crosslinking agent to the matrix.

Contacting the extracellular matrix of the biological tissue with the crosslinking agent does not necessarily results in crosslinking the matrix to a great extent. Frequently, the crosslinking agent needs further activation in order to start or enhance the crosslinking process. When such activation is provided the moldable tissue can be crosslinked thoroughly and to high extent. Moldable tissue which was preliminarily crosslinked to only a small extent after the solubilized extracellular matrix was contacted with the crosslinking agent can be thoroughly crosslinked by provision of activation, in particular heat. Depending on the amount and/or duration of activation the extent of crosslinking can be controlled.

Activation can for example be provided by light such as UV-light, by a chemical activation agent or by heat.

In the following further embodiments relating to the method for preparing a material for medical application are described. These embodiments are particularly suitable for producing a sponge-like material according to the present invention.

According to an embodiment of this method according to the present invention, the solubilized extracellular matrix is transformed into a more concentrated suspension e.g. by centrifugation and removal of surplus supernatant. Further, the suspension with the solubilized extracellular matrix is frozen to form a frozen material. Due to the freezing process, also known as ice templating, a sponge-like (i.e. porous and elastic) material/structure having a low density and high compliancy can be achieved, wherein the forming of the porous structure takes place due to the crystallization of water. Particularly, the generated micro structures can be adjusted by guiding the freezing process accordingly.

Furthermore, according to an embodiment of the method according to the present invention, the frozen material is freeze-dried, particularly for physically stabilizing the generated material.

Furthermore, according to an embodiment of the method according to the present invention, the freeze-dried material is chemically stabilized, particularly by contacting it with a suitable crosslinking agent (e.g. glutaraldehyde) to crosslink the material.

A plurality of crosslinking agents may also be suitable and may contain or consist of carbodiimide, formaldehyde, glutaraldehyde acetals, acyl azides, cyanimide, genipin, tannin, pentagalloyl glucose, phytate, proanthocyanidin, reuterin and/or epoxide compounds. Particularly, according to an embodiment of the method according to the present invention the freezing of the suspension to form a frozen material includes filling the suspension into a porous mold and freezing the suspension residing in the porous mold to form the frozen material, and wherein the porous mold is contacted with a crosslinking agent such that the crosslinking agent contacts and crosslinks the material residing in the mold.

Alternatively, according to an embodiment of the method, freezing the suspension to form a frozen material includes filling the suspension into a mold, freezing the suspension residing in the mold to form the frozen material, and taking the frozen material out of the mold, wherein thereafter the material is freeze-dried for physically stabilizing the material/formed part.

Furthermore, according to an embodiment of the method according to the present invention, after having conducted the freeze-drying of the material, the material is contacted with a crosslinking agent for crosslinking the material.

While the above-described embodiments allow manufacturing a sponge-like material, the method according to the invention also allows forming a material that has denser structure and is suitable for forming e.g. a valve leaflet of a heart valve prosthesis (e.g. TAVI heart valve prosthesis). According to such an embodiment of the method according to the present invention, freezing the suspension to form a frozen material includes spreading the suspension to form a layer and freezing the layer to form the frozen material in the form of a frozen layer, wherein thereafter the layer is freeze-dried and optionally compacted, e.g. by pressing or rolling the layer. After the freeze-drying, the layer (or plate) is contacted with a crosslinking agent for crosslinking the layer.

Particularly, the layer may receive its final shape (e.g. is formed into a valve leaflet or a component thereof) by cutting, particularly laser cutting, or by stamping, or by any other suitable shaping technology.

According to an alternative embodiment of the method, a material layer may also be obtained without freezing the material. Here, the suspension is filled into a container, wherein the suspension is pressed with a porous piston to form a layer, wherein a liquid phase of the suspension escapes via pores of the piston. Thereafter, the layer is contacted with a crosslinking agent to crosslink the layer. Before crosslinking, the layer can be compacted, e.g. by pressing or rolling. Also here, the resulting material/layer can be given its final shape (e.g. forming into a valve leaflet) by cutting, particularly laser cutting, or by stamping (see also above).

Furthermore, the method according to the present invention can also be employed in order to produce a material containing biological tissue in the form of a seamless tube.

According to this embodiment, freezing the suspension to form a frozen material includes filling the suspension into a mold having a tube-shaped cavity and freezing the suspension to form the frozen material in the form of a tube, wherein thereafter the tube is freeze-dried and optionally compacted, e.g. by rolling and/or by applying hydrostatic pressure. Hydrostatic pressing can be achieved by encapsulating the freeze-dried material in an elastic foil and applying a hydrostatic load inside a fluid. After freeze-drying the tube is contacted with a crosslinking agent for crosslinking the tube. Particularly, such a seamless tube can be used as a biological cover of a covered stent.

Furthermore, a further embodiment of the method according to the present invention allows producing a coated base body that is particularly coated in a form-fit manner. Here, in this embodiment, freezing the suspension to form a frozen material includes filling the suspension into a container, immersing a base body in the suspension, taking the base body out of the suspension and then freezing the suspension covering the base body to form the frozen material in the form of a coating of the base body, and wherein thereafter the coating is freeze-dried and contacted with a crosslinking agent for crosslinking the coating. This procedure can particularly be used for coating base bodies in the form of skirts (e.g. of heart valve prostheses, particularly TAVI heart valve prostheses), stents (so-called covered stents), or for biologically functionalizing surfaces (e.g. of medical implants).

According to a further embodiment, the suspension according to the present invention can also be used as 3D printing material. Particularly, according to a further embodiment of the method according to the present invention, the suspension is 3D printed in layers using an additive manufacturing process to form a 3D structure, particularly in form of a medical implant or in form of a component of a medical implant.

Particularly, in an embodiment, the 3D printed structure is contacted upon 3D printing of the structure, or after 3D printing the entire structure with a crosslinking agent to crosslink the structure. According to one aspect of the present invention, the solubilized matrix containing the crosslinking agent or the sponge-like material can be used as seal or sealing device for implants. For this use solubilized matrix containing the crosslinking agent or the sponge-like material can be prepared according to the method described herein. Additionally, it is also possible to use crosslinked as sealing material for implants. Collagen fibers can be acquired from cell cultures and be solubilized and crosslinked. Also, sponge-like material based on crosslinked collagen fibers can be used as sealing material for implants. Accordingly, the present invention is also related to such implants having a moldable tissue suspension based on solubilized extracellular matrix, or crosslinked collagen fibers or sponge-like material based on crosslinked collagen fibers or sponge-like material. Also, it is conceivable that for a heart valve prosthesis a whole assembly of an outer skirt and the leaflet part can be made out of one 3D printed peace being free of any sutures for holding these parts together. Thereby, a heart valve prosthesis is conceivable that merely a structural frame, e.g. a stent, and a valve made of one piece as described above having the outer skirt and the leaflet part together.

Sealing elements as used herein in the field of implants and implantation relate to material and parts of the implants, usually attached to the implant body suitable to reduce or inhibit body liquid flow between the implant and surrounding tissue. Also, sealing elements can relate to material or structural parts of implants suitable to rather tightly cover or fill body cavities or potentially loose parts in the blood flow. Exemplary sealing elements can be used to reduce or inhibit paravalvular leakage around a heart valve prosthesis, cover and seal aneurysms or fix and cover and seal the left atrial appendage and blood clots therein.

According to a preferred embodiment of the present invention, the moldable tissue suspension containing a crosslinking agent is a precursor of the sponge-like material and can be applied as a sealing element to the heart valve prosthesis (e.g. to a biological tissue of the heart valve prosthesis) or at least to one component of the heart valve prosthesis for reducing a paravalvular leakage of the implanted heart valve prosthesis, wherein particularly the moldable tissue suspension is applied to an outside of the heart valve prosthesis which faces the surrounding vessel wall at the implantation site (e.g. at the position of the native valve that is to be replaced), wherein particularly several layers of the suspension are applied to the at least one component of the heart valve prosthesis. It is conceivable that the moldable tissue suspension can be applied also to other implants for the purpose of sealing such as LAA occlude or stent grafts.

Further, in an embodiment, the heart valve prosthesis or the component of the heart valve prosthesis treated with the solution is stabilized and dried (e.g. in a climate cabinet, e.g. at 40° C. and 10% relative humidity, particularly for 12 hours). Stabilized drying significantly contributes to the exceptional swelling behavior of the swellable and sponge-like material.

According to the method, a step of drying is preferably performed after the tissue to be dried has been contacted with stabilizing agents. Suitable stabilizing agents are for example polyols such as glycerol or polyethylene glycols. In a preferred embodiment the tissue to be dried is stabilized with more than one stabilizing agents prior to the drying step. Drying is preferably performed in a drying cabinet at temperatures above room temperature e.g. 40° C.

Further, optionally, hot-pressing is applied to the treated component/tissue. After stabilized drying and hot-pressing the resulting material adopts the significant swelling potential even more as already described herein. Hot-pressing can be preferably conducted at elevated temperature above 40° C. and up to 80° C. and preferably at 60° C. with an applied pressure of about 1 to 7 $N/mm^2$, and preferably 3 to 5 $N/mm^2$ for 10 to 60 minutes and preferably 20 to 40 minutes and most preferably 30 minutes.

By applying the sealing material in form of a suspension to the implant, sewing of other suitable materials like biological tissue (e.g. pericardium) can be omitted, since the extract/solution can be applied in a simple manner and is ready for use after stabilizing and drying it. The obtained material being processed as described herein exhibits similar characteristics as usually used biological materials, e.g. pericardium, and therefore does not exhibit any deteriorated properties and moreover shows a sponge-like behavior as well as a significant increase in thickness upon rehydration after stabilized drying and optional hot-pressing.

According to one aspect of the invention, the solubilized extracellular matrix containing a crosslinking agent according to the invention can also be used as glue and hence to glue for example one or several sealing elements (e.g. out of a tissue) to the surface of a heart valve prosthesis, which also facilitates omitting sewing.

Particularly, according to yet another embodiment of the present invention, the method further includes providing a first and a second member formed out of a biological tissue (particularly porcine or bovine pericardial tissue), wherein the suspension is applied to at least one of the members, and wherein the two members are arranged with respect to one another such that the suspension forms an intermediary suspension layer that contacts both members and is arranged between the two members, and wherein the two members are bonded to one another by contacting the intermediary suspension layer and the members with a crosslinking agent. Optionally the connection can be further mechanically stabilized by applying force to the connection, e.g. pressure. Particularly, the two members can be components of a heart valve prosthesis (e.g. a TAVI heart valve prosthesis). Particularly, each member may form a valve leaflet of a heart valve prosthesis or a component of a valve leaflet.

According to a further embodiment of the method according to the present invention, the method includes providing a first member formed out of a biological tissue (particularly pericardial tissue, particularly native pericardial tissue, particularly porcine or bovine pericardial tissue), wherein the suspension is applied to a surface of the first member, and wherein a second member formed out of sponge-like material, or out of a sponge-like material produced with the method, is arranged on the first member such that the second member contacts the suspension, and wherein the two members and the suspension are contacted with a crosslinking agent to crosslink the suspension and the second member so as to bond the two members together. This provides a structure having a robust carrier material (the biological tissue) carrying a sponge-like material.

Particularly such a structure, e.g. the two members bonded as described above, can be used as a skirt of a heart valve prosthesis (e.g. TAVI heart valve prosthesis) or as a material for such a skirt.

According to yet another aspect of the present invention, a method for preparing a material for a medical application is disclosed, the method including the steps of:
Providing a base body out of a sponge-like material according to the present invention or produced by a method according to the present invention, and
coating the base body with a coating, particularly such that the coating completely encloses the base body.

According to an embodiment of this method, coating the base body with a coating includes arranging the base body in a nutrient solution in the presence of cellulose producing bacteria for forming a cellulose coating of the base body.

Alternatively, according to an embodiment, coating the base body with a coating includes enclosing the base body with at least two members formed out of a biological tissue (e.g. pericardial tissue, particularly native pericardial tissue, particularly porcine or bovine pericardial tissue) which at least to members are bonded together by applying a layer of the suspension described herein between adjacent regions of the members and by contacting the suspension and the members with a crosslinking agent to crosslink the suspension and to therewith bond the members together.

Particularly, such a coated base body can be used as a sealing element of a heart valve prosthesis (e.g. TAVI heart valve prosthesis) against paravalvular leakage, or as an implant on its own, that is particularly implantable via a catheter, for instance. Particularly, the base body may be in the shape of a torus. Also, it is possible to apply the sponge-like material in a spatially defined manner. For instance the moldable suspension can be applied by laying or spraying. In doing so, the geometrical distribution of the sponge-like material can be adapted so as to achieve an optimal sealing. Furthermore, the possibility of shaping/stabilizing the extract/material in three dimensions allows forming complex geometries. In that, specific shapes can be adopted and prepared for the sealing element, which meet best the requirements for the different valve in the human heart. Hence tailor made sealing element for each heart valve can be prepared and provided.

According to a preferred embodiment of the present invention patches of the sponge-like material can be used as sealing material attached on the outside of an implant, e.g. a heart valve prosthesis. In particular those patches can be used in free spaces between the stent struts of the heart valve prosthesis scaffold. Furthermore, the patches can be prepared or cut in the exact form of the free spaces between the struts. Having the form, those patches are perfectly fit for sealing the outer environment of a heart valve carrying scaffold while not occupying to much radial space which is an important feature for TAVI.

Also, the sponge-like material can be sandwiched on the outside of a heart valve prosthesis between the scaffold and an outer skirt. In such an embodiment, it is preferred when the sponge-like material has a form capable of surrounding the scaffold (e.g. a ring, a plurality of patches or a circumferential band). Furthermore, in such an embodiment the sponge-like material is attached to the implant at a position where the implant touches the body tissue at the implanted position. Also, the sponge-like material can be placed in bags or pouches provided on the skirt. In such an embodiment the bags or pouches are filled with a suitable piece or pieces of the sponge-like material and subsequently the bag is closed. The closure can be done either in a sealing manner or in a way that fluid can still get access to the sponge-like material in the pouch or bag. In a further embodiment the sponge-like material can be attached to an implant and preferably to a heart valve prosthesis in an unsymmetrical arrangement such that the sponge-like material is not provided in a circumferential and manner and preferably is only provided at one side of the implant. Such arrangement is advantageous when the implant can be put in place in the body of the patient with a predefined orientation and sealing is only expected or desired at a specific position at the implantation position. By providing the implant only partly with the sponge-like material the volume of the implant can advantageously be reduced.

Furthermore, omitting additional seams by sewing reduces the amount of work and avoids forming additional perforations into the inner skirt of the prostheses for attaching the sealing to the prosthesis.

Generally and as already described above, solubilizing of the tissue facilitates the use of many differently shaped tissues for use in the method. Hence, all kinds of tissue can be used as starting material for the method. Suitable tissue can be of mammalian, including human and also non-mammalian origin and hence non-human origin. In a preferred embodiment the tissue is derived from pig, sheep, goat, horse, crocodile, kangaroo, ostrich, monkey, preferably primate, octopus, rabbit or cattle. Also, in a preferred embodiment the tissue is pericardium, skin, ligament, dura mater, tendons, peritoneum, tela submucosa or pleura.

According to a further embodiment, the sponge-like structures generated with help of the molds are applied to the heart valve prosthesis as a sealing material for reducing a paravalvular leakage of the implanted heart valve prosthesis.

According to one aspect of the invention sponge-like material is based on and originates from biological material. In that aspect a sponge-like material including or consisting of or is derived from or is made of extracellular matrix and is elastic and exhibits a water content of 80 to 99% w/w and 40 to 90 compressibility units [CU]. In this regard, the compressibility of a material is quantified by putting a test cylinder of 20 mm diameter and 150 g weight for 30 seconds to a specimen of minimum 15 mm thickness. The compressibility in compressibility units (CU) is given by the following formula: Compressibility=100×(depth of indentation)/15 mm [CU]. The material is crosslinked by a suitable crosslinking agent. In a preferred embodiment the material is decellularized. Also, the material is free or substantially free of α-gal epitopes.

A major advantage of the sponge-like material as provided herein resides in the elasticity of the material, even in or starting from wet state. The material is capable of increasing its volume multifold times when applied pressure is released from the material. Thereby, the sponge-like material can be used on implants, for instance as sealing material for paravalvular leakages, which are wet stored. Hence, for the preparation of the implant the step of drying the sealing material becomes moot. Moreover, the sponge-like material can be based on known biocompatible biological tissue which has been used in patients in the past without evoking inflammatory reactions due to repulsion. Hence, by the present sponge-like material a non-artificial elastic material can be provided which is well suitable for implantation. Also, the sponge-like material is free of any synthetic or non-biological polymeric material.

In one embodiment, the sponge-like material as provided herein exhibits 40 to 70 compressibility units [CU], meaning that the material is to smaller extent elastic. Such material, when applied as sealing material for paravalvular leakage, is in particular suitable for smaller expected leakage. Such case can occur when the malfunctioning original heart valve is still consisting of soft tissue and adopts a rather "normal" geometry.

In a further embodiment sponge-like material as provided herein exhibits 65 to 90 compressibility units. Such material, when applied as sealing material for paravalvular leakage, is in particular suitable for rather large expected paravalvular leakage. Such case can occur when the malfunctioning original heart valve is rather consisting of harder tissue due to strong calcification and may adopt a rather "unusual" geometry.

According to a further aspect of the present invention, a heart valve prosthesis is provided, having sealing material for reducing a paravalvular leakage of the implanted heart valve prosthesis, wherein the material is based on biological tissue that has been prepared using the method according to the invention as described herein or has the properties of the sponge-like material as provided herein.

Also, the present invention is directed to a heart valve prosthesis having sealing material for reducing a paravalvular leakage heart valve prosthesis, wherein the sealing material was applied to an implant, preferably a heart valve prosthesis, preferably in several layers by spraying, spreading, dipping, electro spinning and/or liquidly depositing.

Spreading may comprise applying the sealing material e.g. by a brush, a piece of cloth or other technique suitable to apply a liquid medium in small doses to a large surface. Liquidly depositing may include applying the sealing material e.g. by needle or cannula to the desired surface.

According to a further aspect of the present invention, the solubilized extracellular matrix containing a suitable crosslinking agent can be used as precursor for sealing material on implants, in particular on heart valve prostheses or occluding devices. Also the present invention is directed to the use of the solubilized extracellular matrix containing a suitable crosslinking agent as glue in the medical field, in particular as glue on implants or as glue for surgical incisions. Also the present invention is directed to the use of sponge-like material as characterized herein as sealing material for implants as described herein. In particular, the sponge-like material can be used as sealing material on heart valve prosthesis or venous valve prosthesis to reduce or inhibit paravalvular leakage. Also, the sponge-like material can be used as sealing material for LAA occluder. Further, the sponge-like material can be used as filling material for aneurisms or other cavities in the body due to disease or surgery. Moreover, the sponge-like material as provided herein can be used as annular paving device or part thereof. An annular paving device can be sponge-like material in ring shape and be implanted e.g. on the natural malfunctioning valve as an additional sealing device when the heart valve prosthesis is implanted. Also, the sponge-like material can be prepared having the shape of a tube that can be mounted on a stent. Such an endovascular stent graft covered with the sponge-like material can be deployed at the site of an aneurism to help prevent rupture of the vessel. In particular, such a stent graft has the advantage of a sealing material with is elastic, but can simultaneously provide biocompatibility to avoid further irritations at the site of the aneurysm.

Furthermore, according to yet another aspect of the present invention, an implant is disclosed (e.g. in the form of heart valve prosthesis, particularly TAVI heart valve prosthesis, or in the form of a stent, particularly a covered stent), including at least one of:

a layer, particularly forming a valve leaflet or a component thereof, produced with the method described herein, a tube, particularly forming a cover of the implant (wherein the implant is e.g. a covered stent), wherein the tube is produced with the method described herein, a base body coated with a coating using the method described herein, a first and a second member bonded together according to the method described herein, wherein particularly the first and the second member form components of an implant in the form a heart valve prosthesis, particularly a TAVI heart valve prosthesis, a material produced using a method according to the present invention.

EXAMPLES

Example 1

In the following an exemplary process for manufacturing an extract from decellularized biological tissue (e.g. based on porcine pericardium) and its application to a TAVI heart valve prosthesis is described, in which the resulting material undergoes a significant increase in thickness upon rehydration (at the implantation site).

Figure 1:
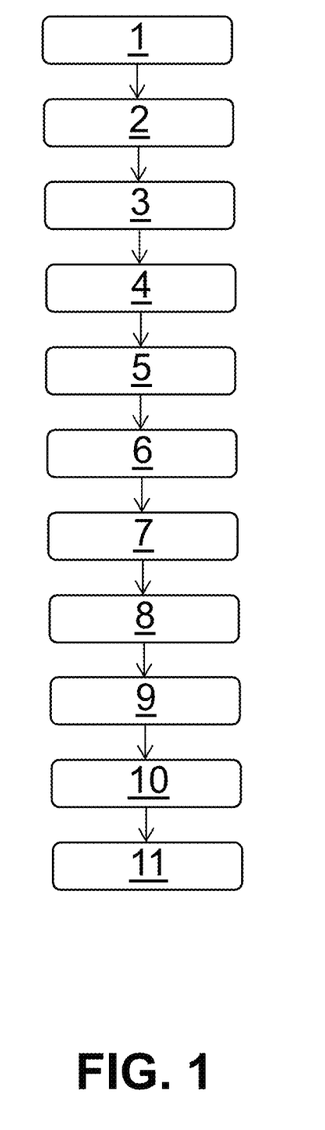
FIG. 1 shows a block diagram of an exemplary method according to the present invention and as further described in Example 1.

The individual succeeding steps of this example of the method according to the invention are depicted in FIG. 1

In step 1, porcine pericardium is harvested from a pig at a slaughterhouse and is stored in isotonic saline solution (0.9% w/v; Fresenius-Kabi) at a temperature of 4° C. for 2-6 hours. The solution contains sodium chloride as well as penicillin and/or streptomycin to prevent bacterial growth.

In step 2, the tissue is prepared, moist, in isotonic saline solution (0.9% w/v; Fresenius-Kabi). That is, the layers of the pericardium are separated from one another, adhering fatty and connective tissue is carefully removed, and the tissue is cut to the size and shape for the desired application.

After rinsing for 5 minutes with an isotonic saline solution (e.g. 100 ml 0.9% w/v; Fresenius-Kabi) with slight movement of the tissue in step 3, the tissue is decellularized in step 4.

The decellularization in step 4 takes place with a detergent buffer solution containing surfactin. In this exemplary embodiment of the invention, surfactin (Sigma-Aldrich, surfactin from *Bacillus subtilis*, Catalog #S3523) having a concentration of 0.06% w/v is dissolved in isotonic saline solution (0.9% w/v; Fresenius-Kabi) in the presence of 0.5% w/v sodium deoxycholate (Sigma-Aldrich, deoxycholic acid, Catalog #D6750). The tissue remains in this solution e.g. for 20 hours at 37° C. During this treatment, tissue is cleaned nearly entirely of cellular components located therein without substantially changing the structure of the collagen fibers. As also stated above, decellularizing with deoxycholate and surfactin processes tissue in a gentle manner in order to remove cellular components so as to get the pure extracellular matrix composed predominantly of collagen und elastin.

Alternatively, the tissue can be decellularized with 0.5% w/v SDS in isotonic saline solution (0.9% w/v; Fresenius-Kabi), for a time span of 24 h at 37° C. By treating the pericardium tissue with the strongly denaturing detergent SDS the collagen und elastin are additionally changed in a structurally irreversible manner. Spiral structures are dissolved and rod shaped proteins are formed which have a larger average length.

In step 5 the tissue is rinsed in 100 ml isotonic saline solution (0.9% w/v; Fresenius-Kabi) at room temperature with slight movement. Step 5 is repeated here in this exemplary embodiment of the invention 8 times for 10 minutes for removing the residual detergent.

Thereafter in step 6, the tissue is solubilized e.g. by acidic digestion in 1 N HCl for 12 h with subsequent neutralization using NaOH, centrifugation to obtain the constituents of solubilized extracellular matrix and resuspension of the pellet in 0.9% w/v NaCl to obtain a concentrated solution of the tissue extract.

Alternatively, the tissue is solubilized by enzymatic disintegration e.g. by 4 U/ml collagenase type IV from *clostridium histolyticum* (Biochrom, Catalog #C4-28) for 12 h in a 50 mM TES buffer (AppliChem, Catalog #A1084) containing 10 mM Ca, centrifugation to obtain the constituents of solubilized extracellular matrix and resuspension of the pellet in 0.9% w/v NaCl to obtain a concentrated solution of the tissue extract.

Alternatively, the extracellular matrix can be solubilized by wet mechanical homogenization by grinding the extracellular matrix into a suspension using a homogenizer (Bertin, Precellys Evolution) and ceramic pellets (Bertin, Catalog #CK14) in 0.9% w/v NaCl, in doing so the tissue is cooled during homogenization.

Alternatively, the tissue is mechanically solubilized in the solid state e.g. by homogenization of the frozen extracellular matrix: e.g. by liquid Nitrogen in the form of comminuting the frozen extracellular matrix by grinding (Bertin, Precellys Evolution with ceramic pellets (Bertin, Catalog #CK14)) or manually pestling, thawing of the comminuted extracellular matrix and resuspension in 0.9% w/v NaCl.

Preferably, the solubilizing step is continued until small tissue parts or tissue fibers having a sufficient and/or desired average size are obtained. Particles in micro meter range can easily be obtained.

Manufacturing of a desired particle or fiber size can be done in all four variants in an optimal fashion. As already explained herein, having predominantly long and linear tissue fibers is ideal for having an optimal sponge-like material and a maximal swelling capacity.

Then, in step 7, the solubilized extracellular matrix is contacted with crosslinking agent (here glutaraldehyde) to form a diluted solution. This can be done by diluting the tissue extract in DPBS without Ca and Mg (Lonza, Catalog #17-512Q) and adding the glutaraldehyde (Sigma-Aldrich, glutaraldehyde solution, Catalog #G7651), preferably provided in a concentration of 0.08-1% w/v.

Further, in step 8, this solution is heat treated for 1 hour at 40° C. in a heat cabinet to form a high concentration of free aldehyde groups within the solubilized extracellular matrix exhibiting a moldable tissue suspension with activated precursors. The step of forming a high concentration of reactive aldehyde groups within the solubilized extracellular matrix can be optimized by fine tuning the reaction temperature, the concentration of the glutaraldehyde and the reaction time.

Thereafter, in step 9 the suspension of step 8 is applied in several layers to a TAVI heart valve prosthesis, e.g. by laying it on, spraying it on or by immersing the heart valve or a specific component thereof, preferably the skirt tissue of the prosthesis, in the solution. Alternatively, the suspension can be applied by a cannula, a needle or a brush. Between applying two succeeding layers an intermediate heat processing may be conducted at 60° C. for activating the chemical crosslinking. Depending on the crosslinking agent alternative activation such as UV light, chemical activators and the like can be applied.

In a further embodiment, in process step 9, already chemically activated tissue fibers are applied, e.g. layer by layer on a heart valve prosthesis (e.g. TAVI prosthesis).

Further, in step 10, the tissue obtained in step 9 is stabilized with glycerol and polyethylene glycols and dried in a climate cabinet. This can be done e.g. by subsequently rinsing the material with aqueous solutions of 20% v/v glycerol (37° C., 2 hours), 20% v/v polyethylene glycol (mean molecular weight 400 g/mol, 37° C., 2 hours), 20% v/v polyethylene glycol (mean molecular weight 6000 g/mol, 37° C., 2 hours) accompanied by gentle movement and drying in a climate chamber at 40° C. and 10% relative humidity for 12 hours. Optionally the dried material undergoes hot-pressing at 60° C. with an applied pressure of about 3 N/mm² for 30 minutes if that is technically realizable on the heart valve prosthesis.

Finally, in step 11 the heart valve prosthesis is mounted on a catheter and is sterilized by e.g. standard ethylene oxide (EtO) treatment.

Example 2

For example 2 steps 1 to 6 are conducted as described in example 1. Subsequent steps are conducted in a different way in order to obtain a solid three-dimensional object composed entirely of the sponge-like swellable material as described herein.

The solubilized extracellular matrix obtained in step 6 is at first centrifuged (3.000 g for 10 minutes) and the supernatant is discarded. The tissue fibers are then immersed in DPBS without Ca and Mg (Lonza, Catalog #17-512Q) and are formed into a homogeneous and viscous suspension of defined concentration by vortexing and mixing. Thereafter, the resulting suspension is mixed with glutaraldehyde (Sigma-Aldrich, glutaraldehyde solution, Catalog #G7651) such that glutaraldehyde will have a concentration of 0.08-1% w/v. The resulting moldable suspension is then filled into a mold that is covered in order to prevent evaporation. The crosslinking is done without further movement at e.g. 60° C. for three days.

The resulting mold can then be dried after stabilization and optionally hot-pressed as in step 10 of example 1 to obtain a sponge-like swellable material.

The obtained material is solid and can be optionally cut into any desired shape using e.g. scissors or scalpels. The resulting material can be attached to a TAVI heart valve prosthesis, e.g. by sewing to the metallic stent or tissue, e.g. preferably the skirt material.

Finally the heart valve prosthesis is mounted on a catheter and is sterilized by e.g. standard ethylene oxide (EtO) treatment as in step 11 of example 1.

Example 3

For example 3 steps 1 to 7 are conducted as described above. Subsequent steps are conducted in a different way in order to obtain a sponge-like swellable material as described herein.

The moldable tissue suspension obtained in step 7 is at first centrifuged (3.000 g for 10 minutes) and the supernatant is discarded. The obtained tissue fibers are mechanically mixed to get a rigid plasticized material. This highly viscous material can be arranged in a mold and can thus be structured three-dimensionally. An additional pressing step is optional. The obtained structures are dimensionally stable and are permanently stabilized using crosslinking with 0.08-1% w/v glutaraldehyde (Sigma-Aldrich, glutaraldehyde solution, Catalog #G7651) in DPBS without Ca and Mg (Lonza, Catalog #17-512Q) at e.g. 60° C. for three days.

The resulting mold can then be dried after stabilization and optionally hot-pressed as in step 10 of example 1 to obtain a sponge-like swellable material.

The obtained material is solid and can be optionally cut into any desired shape using e.g. scissors or scalpels. The resulting material can be attached to a TAVI heart valve prosthesis, e.g. by sewing to the metallic stent or tissue, e.g. preferably the skirt material.

Finally, the heart valve prosthesis is mounted on a catheter and is sterilized by e.g. standard ethylene oxide (EtO) treatment for dried tissue as in step 11 of example 1 or a liquid sterilization process for wet tissue.

Example 4

For example 4 steps 1 to 5 are conducted as described above. Subsequent steps are conducted in a different way in order to obtain a sponge-like swellable material as described herein.

Step 6 of example 1 can be conducted as described above, preferably the tissue is solubilized by wet grinding the extracellular matrix into a suspension using a homogenizer (Bertin, Precellys Evolution) and ceramic pellets (Bertin, Catalog #CK14) in DPBS without Ca and Mg (Lonza, Catalog #17-512Q); in doing so the tissue is cooled during homogenization. In particular, tissue pieces of about 400 mg wet weight are obtained, placed into 7 ml tubes (Bertin, Catalog #KT03961-1-307.7) and 5 ml/g of DPBS without Ca and Mg (Lonza, Catalog #17-512Q) are added. The material is homogenized for e.g. about 20-30 times at 8800 rpm for 10-20 seconds. Between the homogenizing steps the samples are cooled, e.g. in an ice bath, until the temperature is below 8° C. to avoid denaturation. Preferably, the homogenization is continued until small tissue parts or tissue fibers having a sufficient and/or desired average size are obtained.

Thereafter, the obtained extracellular matrix suspension is freed from any bubbles e.g. by placing the solubilized material onto a horizontal shaker with moderate movement at 37° C. for 15 min or by stirring (e.g. 300 rpm for 30 min). Optionally the tissue suspension can be concentrated to enhance the viscosity by applying heat, e.g. 50° C., during de-bubbling.

Further, the moldable and viscous tissue suspension is filled into molds using a 1 ml pipette and thus may be structured three-dimensionally. Preferably, the molds are semi-permeable with a pore size below the average size of the obtained fibers in the tissue suspension and above the size of a glutaraldehyde monomer, respectively. Additionally, the inner surface of the molds is preferably smooth to obtain a smooth surface of the resulting material. As molds can be used e.g. PTFE hoses, wire meshes with 10 µm mesh aperture or wire meshes with larger mesh aperture lined in with a polymer membrane.

The mold is put into a container and contacted with the crosslinking solution containing 0.08-1% w/v glutaraldehyde (Sigma-Aldrich, glutaraldehyde solution, Catalog #G7651) in DPBS without Ca and Mg (Lonza, Catalog #17-512Q). The crosslinking solution has to be applied slowly in order to avoid agitation and the mold should cover the tissue suspension to avoid dilution. After applying the crosslinking solution the mold together with the crosslinking solution is frozen at e.g. −25° C. for 2 to 8 days. The mold with the tissue extract as well as the crosslinking solution can additionally be cooled to e.g. 4° C. prior to application in order to achieve a fast freezing.

Figure 2A:
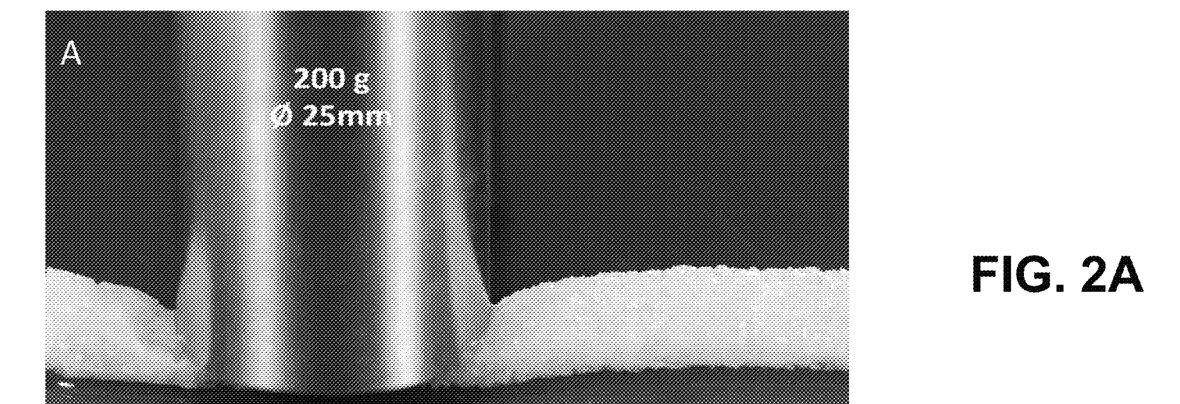
FIG. 2A shows an exemplary piece of the sponge-like material (rod with 8 mm diameter) consisting of porcine pericardium prepared as described in example 4. Further in 2A on the left an external load of 200 g (25 mm diameter) compresses the material to about 1 mm. In the lower FIG. 2B the sample is shown 15 seconds after the applied external load was removed. The initial sample geometry is fully recovered, showing the sponge-like properties.
Figure 2B:
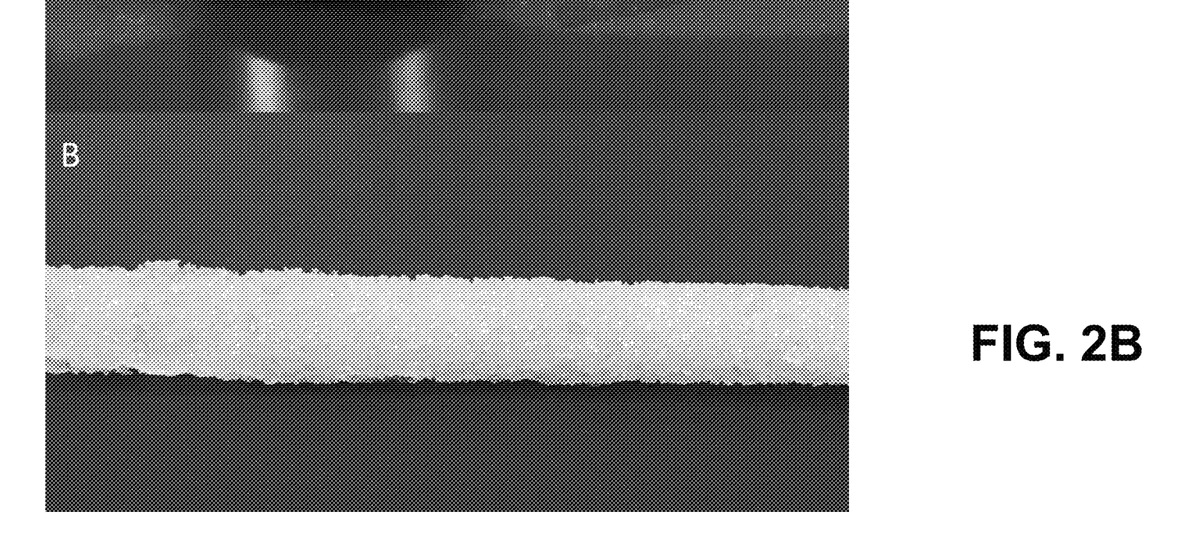

Thereafter, the molds are thawed at e.g. room temperature. The obtained structures are dimensionally stable and are permanently stabilized by subsequent crosslinking with 0.08-1% w/v glutaraldehyde (Sigma-Aldrich, glutaraldehyde solution, Catalog #G7651) in DPBS without Ca and Mg (Lonza, Catalog #17-512Q) at e.g. 60° C. for three days. The resulting material shows a sponge-like behavior, i.e. the material can be compressed easily and resembles its shape after releasing the compression under wet conditions. FIG. 2 shows such a sponge-like material made from porcine pericardium in the shape of a rod with 8 mm diameter. On the left an external load of 200 g (25 mm diameter) compresses the material to about 1 mm.

The resulting mold can then optionally be dried after stabilization and optionally hot-pressed as in step 10 of example 1 to obtain a sponge-like swellable material, which undergoes a significant increase in its width upon rehydration.

The obtained material is solid and can be optionally cut into any desired shape using e.g. scissors or scalpels. The resulting material can be attached to a TAVI heart valve prosthesis, e.g. by sewing to the metallic stent or tissue, e.g. preferably the skirt material. Alternatively, it is possible to sew tissue pockets from e.g. porcine pericardium and put the obtained sponge-like material inside.

Finally, the heart valve prosthesis is mounted on a catheter and is sterilized by e.g. standard ethylene oxide (EtO) treatment for dried tissue as in step 11 of example 1 or a liquid sterilization process for wet tissue.

Example 5

The resulting material of examples 1, 2, 3 and 4 are particularly suitable for being used and/or inserted into a separate 'annular paving device', which means that a separate device prior to TAVI implantation is placed in the annulus of the patients.

The exemplary embodiments described above are intended to clarify the invention. The number and/or design of the process steps (in particular the concentrations, the composition of the buffers and solutions for crosslinking and rinsing) can be varied by a person skilled in the art.

Example 6

Particularly, in the following embodiments, non-treated or pre-treated biological tissue is comminuted in a first step by mechanical comminution. By means of the way and degree of the comminution properties of the homogenate (e.g. suspension) can be adjusted, wherein the molecular composition as well as the molecular properties of the starting material can be maintained. In a second step, a new material is formed out of the homogenate which is then chemically stabilized, e.g. by crosslinking (e.g. contacting the material with a crosslinking agent).

Particularly, in a first step, which relates to producing a homogenate, 1) porcine pericardial tissue is comminuted with surgical scissors into 5 mm×5 mm large pieces and is put into a plastic container together with DPBS and ceramic balls,
2) subsequently, the tissue is mechanically comminuted in a homogenizer by shaking movements while maintaining a maximum temperature, wherein the tissue is cooled upon comminuting the tissue in the homogenizer.
3) The suspension generated in this way is separated from the ceramic balls and can be diluted—according to the desired properties for further processing—by adding DPBS. Furthermore, the suspension may be concentrated by centrifugation.

Furthermore, particularly, in a second step, the material may achieve a certain shape.

a) For instance, a sponge-like (e.g. porous and elastic) material/structure may be achieved by using ice templating. This allows one to generate porous and elastic structures having a low density and high compliancy. For this, the suspension generated in the first step is filled into a mold and frozen. The forming of a structure takes place due to the crystallization of water, wherein the generated micro structures can be adjusted by guiding the freezing process accordingly (e.g. regarding velocity and direction etc.) and optionally by adding further substances to the suspension (e.g. salts, DMSO, alcohols). This allows one to define the micro structure and the shape of the surface of the material/structure. This material/structure can be permanently chemically stabilized in different ways, e.g.

I) by using a porous mold, a substance for chemically stabilizing the material, particularly glutaraldehyde, is brought into contact with the frozen material/formed part and is thereby stabilized. The chemical crosslinking takes place in the mold.

II) the mold is formed by the frozen substance for stabilization. Here, no extraneous material is involved and the crosslinking is performed as in I).

III) The frozen material/formed part is taken out of the mold and is physically stabilized by freeze-drying the material. Thereafter, the material is chemically stabilized by adding the crosslinking agent.

b) Furthermore, alternatively, a dense structure for e.g. realizing a valve leaflet of a heart valve prosthesis, particularly a TAVI heart valve prosthesis (wherein TAVI stands for Transcatheter Aortic Valve Implantation), I) can be produced by spreading the suspension formed in the first step (see above) to form a layer of homogeneous thickness which is then frozen and freeze-dried. Thereafter, the physically stabilized layer/plate is particularly compacted by pressing or rolling. Then, the layer is chemically stabilized by adding a cross linking agent. The final shaping of the layer can be performed by laser cutting or stamping the layer or by other suitable methods.

II) Alternatively, the suspension can be filled into an open mold. Then, the suspension is pressed with a porous piston to compact the suspension, wherein a liquid phase of the suspension can escape through pores of the piston. Optionally, the generated part can be compacted by pressing or rolling it. Thereafter, the part is chemically stabilized by adding a crosslinking agent. The final shaping of the part can be done by laser cutting or stamping or the like.

c) Furthermore, alternatively, a seamless tube out of biological material can be produced, by filling the suspension generated in the first step into a correspondingly shaped mold, freezing it and freeze-drying it. Then, the physically stabilized tube can be compacted by rolling it or by hydrostatic pressure. Thereafter, the tube is chemically stabilized by adding a crosslinking agent. In this way, a seamless tube can be constructed. Such a tube can be used as a biological cover of a covered stent.

d) Furthermore, alternatively, a base body can be coated in a form-fit manner, by filling the suspension generated in the first step into an open container. The base body to be coated is immersed in the suspension, taken out and then frozen. This process can be repeated in order to achieve a defined thickness of the coating which can also be defined by the properties of the suspension. Thereafter, the coated base body is chemically stabilized e.g. by immersing it in a crosslinking agent. In this way a cover enclosing the base body is produced that has a pre-definable micro structure out of a biological material, which may also fill the cells between struts of the base body (e.g. stent). Application examples are skirts for (e.g. TAVI) heart valve prostheses, covered stents or the biological functionalization of surfaces.

e) Furthermore, alternatively, instead of using a mold, the shaping/forming of the structure can also be achieved by way of 3D printing the suspension. Here, as a printing material, the suspension generated in the first step is used or a modified suspension, which may include stabilizers, e.g. for maintaining printability. 3D printing can be conducted by way of additive manufacturing. Chemical stabilization can be achieved during the 3D printing process, e.g. by locally applying a crosslinking agent, or thereafter (e.g. application of a crosslinking agent to the entire 3D printed structure).

The particular advantages of the above-described embodiments are the possibility to produce implants that have a biological tissue part, which has spatially homogeneous properties. Essential advantages can be seen in maintaining the biological properties of the tissue part although the latter has a modified micro structure. This renders the manufacturing process of implants more effective and cost-efficient. Furthermore, the individual products/implants become more uniform concerning their properties. Moreover, new implants can be generated such as a covered stent having improved blood compatibility. In principle, the universal technology according to the present invention can be applied in the field of structural heart implants.

Example 7

Furthermore, the invention also relates to forming a covalent chemical bond in order to seamlessly bond to biological materials together.

Also this example is based on the suspension formed in the first step of Example 6 listed above.

a) Here, the solution can be used to bond e.g. porcine pericardial tissue (e.g. of a TAVI heart valve prosthesis). Particularly, the homogenate/suspension is applied between two members, each formed by a native pericardial tissue patch. By adding a crosslinking agent/solution, e.g. 0.5% glutaraldehyde in DPBS, a permanent covalent bond is achieved between the pericardial tissue patches and the suspension. Optionally, a mechanical stabilization of the connection region can be achieved by e.g. pressing the connection region. The resulting bond between the patches is seamless and load-bearing.

b) Furthermore, a hybrid skirt of pericardial tissue and sponge-like biological material for an (e.g. TAVI) heart valve prosthesis can be formed by providing a first member out of e.g. native pericardial tissue on which a layer of the homogenate/suspension generated in the first step of Example 6 is applied. A freeze-dried sponge-like material that has been generated as described above but has not been chemically stabilized yet is arranged on top of the suspension layer. Thereafter, chemical stabilization is carried out by adding a crosslinking agent. In this way a structure out of a robust carrier material and a highly elastic, sponge-like material can be achieved which may optionally be structured in a lateral fashion. By orienting the sponge-like material towards the outside of the prosthesis and improved sealing of leakages can be achieved.

c) Furthermore, a sealing ring having a sponge like structure for reducing para-valvular leakages can be formed by:

I) providing a sponge-like material produced as described above, which is then cultured in a nutrient solution in the presence of cellulose producing bacteria so as to coat the sponge-like material with cellulose. This generates a dense, form-fit connection between the cellulose cover or coating and the sponge-like core. By this method a torus shaped sealing ring for a TAVI heart valve prosthesis can be produced.

II) instead of a cover/coating out of cellulose also a cover or coating made from seamlessly bonded pericardial tissue, as described above in point a) can be used.

d) Finally, in an analogous fashion to the two methods for generating a sealing ring described in point c), arbitrary three-dimensional formed parts can be generated. Due to the high elasticity of these formed parts the letter can be positioned by a catheter system, for instance in order to fill hollow spaces. Possible applications are:

I) stabilization of aneurysms in the vascular system,
II) sealing of septal defects,
III) sealing of leakages of implants by secondary implantation of sealing material, e.g. in the form of plugs,
IV) implantation into the human body for purposes of cosmetic surgery, e.g. in the form of breast implants.

Due to the core-cover structure the application of biological materials as a core material is possible which could otherwise not be used in vascular implants, e.g. due to release of particles, mechanical instability or limited long time stability. Furthermore by choosing a suitable cover or coating material the implant properties can be improved significantly regarding the biological interaction. By using a homogenate in combination with a cross-linking agent a seamless, permanent connection of biological materials can be achieved. This universal technology opens new possibilities for future applications in the field of structural heart implants.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention claimed is:

1. A method for preparing dimensionally stable material for a medical application, the method comprising the steps of:
   providing an extracellular matrix from biological tissue,
   decellularizing the extracellular matrix through decellularizing solution to obtain an acellular extracellular matrix,
   solubilizing the acellular extracellular matrix to create a moldable suspension,
   filling the suspension into a mold and cross-linking the suspension with a cross-linking agent at temperatures below 0° C. for a period of more than 12 hours without movement of the moldable suspension to form a cross-linked matrix to the mold,
   thawing the mold and the cross-linked matrix at room temperature to obtain the dimensionally stable material.

2. The method according to claim 1, wherein solubilizing the extracellular matrix of the biological tissue comprises one of:
   chemical solubilizing the extracellular matrix,
   enzymatic solubilizing the extracellular matrix,
   wet mechanical solubilizing the extracellular matrix, and
   dry mechanical solubilizing the extracellular matrix in the solid state.

3. The method according to claim 1, comprising hot pressing the dimensionally stable material.

4. The method according to claim 1, further comprising providing a first and a second member formed out of a biological tissue, wherein the moldable suspension is applied to at least one of the members, and wherein the two members are arranged with respect to one another such that the moldable suspension forms an intermediary layer that contacts both members and is arranged between the two members, and wherein the two members are bonded to one another by contacting the intermediary layer and the members with a cross-linking agent.

5. The method according to claim 2, wherein the chemical solubilizing comprises acidic digestion, the enzymatic solubilizing comprises disintegration with enzymes, and the dry mechanically solubilizing comprises first freezing the extracellular matrix and comminuting the frozen extracellular matrix and subsequently thawing and suspending of the comminuted extracellular matrix.

6. The method according to claim 5, wherein the enzymes comprise a collagenase type IV enzyme.

7. The method according to claim 1, wherein the mold is porous or semipermeable.

8. A method for preparing material for medical application,
   the method comprising the steps of:
      obtaining an extracellular matrix from biological tissue,
      solubilizing the extracellular matrix to form a suspension,
      filling the suspension into one or more molds,
      contacting the suspension with crosslinking solution,
      freezing the one or more molds at temperature below 0° C. for a period of more than 12 hours without movement of the suspension and without freeze-drying, and
      thawing the one or more molds once to release one or more dimensionally stable structures.

9. The method according to claim 1, wherein the cross-linking agent is glutaraldehyde.

10. The method according to claim 1, wherein the mold is formed by a frozen substance for stabilization.

11. The method according to claim 8, wherein the cross linking agent is glutaraldehyde.

12. The method according to claim 1, comprising permanently stabilizing the dimensionally stable material by subsequent cross-linking.

13. The method according to claim 12, wherein the subsequent cross-linking is carried out by using a glutaraldehyde solution.

14. The method according to claim 1, comprising drying the dimensionally stable material.

* * * * *